United States Patent [19]

Peters et al.

[11] 4,238,337
[45] Dec. 9, 1980

[54] METHANE GAS PRODUCER USING BIOLOGICAL DECOMPOSITION OF WASTE MATTER

[75] Inventors: Melville F. Peters, Livingston, N.J.; Walter T. Peters, East Dennis, Mass.

[73] Assignees: Walter Todd Peters; Margot Elizabeth Peters, both of East Dennis, Mass.; Albert F. Kronman, Locust Valley, N.Y.

[21] Appl. No.: 10,689

[22] Filed: Feb. 9, 1979

[51] Int. Cl.³ .............................................. C02F 1/00
[52] U.S. Cl. .................................. 210/179; 210/180; 210/188; 210/532.1; 435/289; 435/312; 435/316
[58] Field of Search ............... 435/312, 316, 291, 290, 435/289, 249, 250, 277, 801, 166, 167; 210/149, 179, 180, 187, 188, 532 R

[56] References Cited

U.S. PATENT DOCUMENTS

| 3,175,688 | 3/1965 | Zink | 435/290 X |
| 3,981,803 | 9/1976 | Cowlthard | 435/801 X |
| 4,019,962 | 4/1977 | Allen | 435/316 X |
| 4,057,401 | 11/1977 | Boblitz | 435/801 X |

Primary Examiner—R. B. Penland
Attorney, Agent, or Firm—Albert F. Kronman

[57] ABSTRACT

A container for holding organic waste matter while it is being decomposed biologically to produce methane gas and other products. The container also houses one or more paddlewheels which stir the waste matter and assist in maintaining it at constant, elevated temperature. Temperature control means include a temperature sensor, heating pipes, and two external heat exchangers for stabilizing the temperature of the waste material. In addition, a two-way valve (controlled by the temperature sensor) switches liquid in the heating pipes from one heat exchanger to the other to maintain the predetermined operating temperature.

4 Claims, 6 Drawing Figures

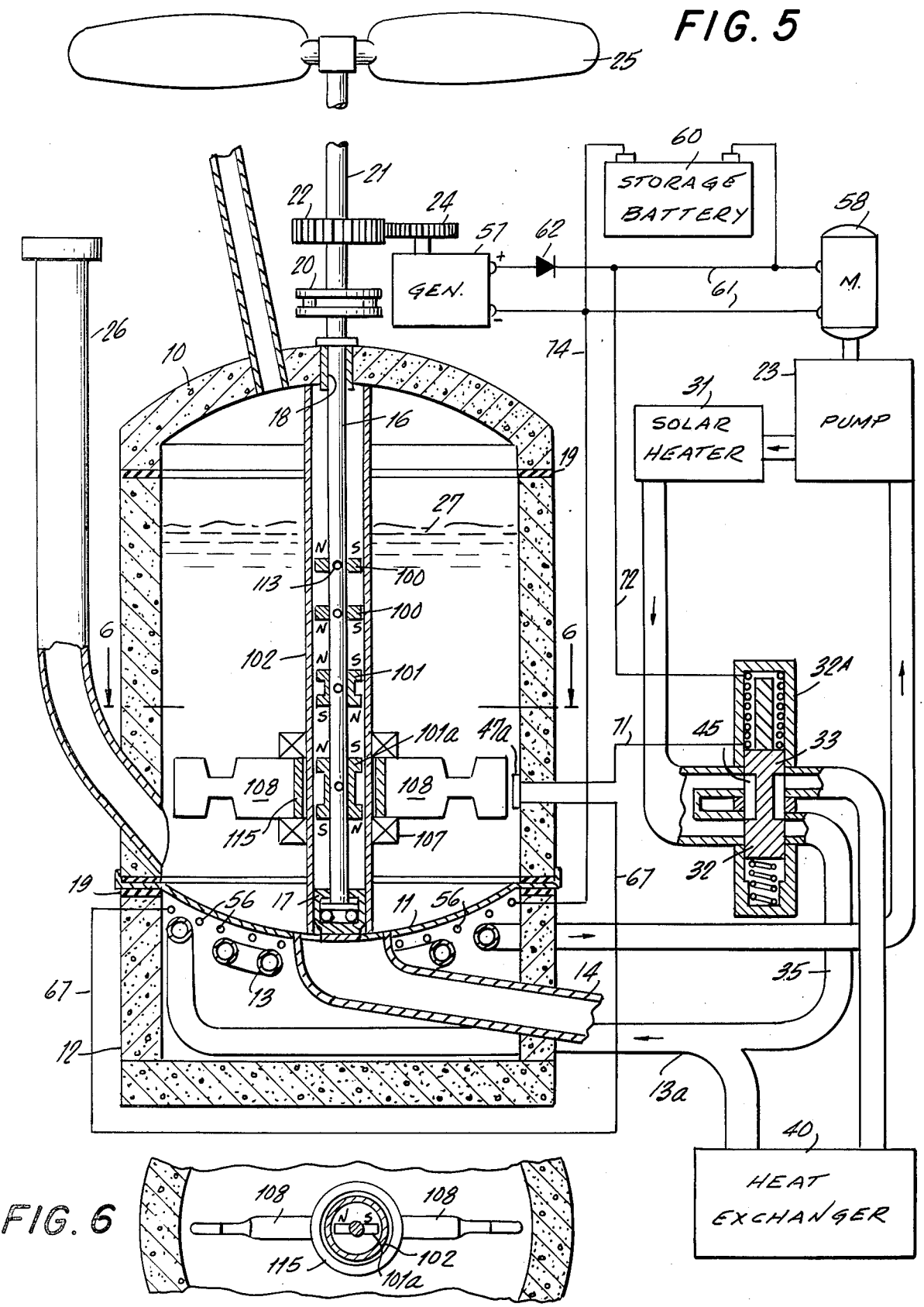

METHANE GAS PRODUCER USING BIOLOGICAL DECOMPOSITION OF WASTE MATTER

BACKGROUND OF THE INVENTION

The biological fermentation process which produces methane and other gases from sewage and other organic waste materials is a natural process and can operate without the help of man-made apparatus. The use of suitable apparatus, however, can speed up gas production, make the process more efficient, and provide storage means for the combustible gases. An ideal process which can use anerobic bacteria for the production of methane includes the use of sewage, garbage, and cellulose waste products as basic materials. The process also preferably includes the use of solar energy and wind energy to heat the generating mass to an optimum termperature which lies within the range of 85° F. to 95° F. (29.5° C. to 35° C.).

In order to maintain a proper temperature throughout the day and night in northern countries during the winter months, it is necessary to combine the radiant energy from the sun with some other form of energy. The additional energy may be derived from heat exchangers operated by burning methane, natural gas, etc. or by using wind power to move paddles within the operating slurry to generate heat by mechanical friction. The use of paddlewheels in the slurry also serves to break up any encrusted solid material which may be moved to the surface of the slurry, bouyed up by the minute bubbles of generated gas. The paddlewheel motion releases the bubbles and permits the encrusted material to sink to the bottom of the tank. The fully digested material can then be drawn periodically from the bottom of the container and used as fertilizer. An arrangement of temperature control units, to be described in detail later, is used to maintain an optimum operating temperature automatically and to make full use of solar energy.

One of the features of the present invention is the apparatus which automatically adjusts for an optimum termperature in the digester container.

Another feature of the invention is the use of radiant energy from the sun to heat the slurry in the digester container.

A further feature of the invention is the use of a plurality of paddlewheels turned by wind power, to add frictional heat to the slurry.

Still another feature of the invention is the use of magnetic eddy currents to provide heat for the digester slurry.

SUMMARY

The invention comprises an apparatus for the production of methane gas by biological decomposition of waste matter and includes a container for storing the waste during the decomposition process. A conduit is provided for admitting additional waste material to the bottom of the container and an outlet pipe is provided at the top of the container for drawing off the generated gas. A rotatable paddlewheels assembly, operated by wind power, is positioned within the container and operates to break up the digested crust floating on top of the waste material. The paddle assembly also separates the gasbubbles from the floating particles so they can sink to the bottom of the container. A thermostat maintains the waste material at an optimum temperature by the use of a temperature sensor and a two-way valve controlled by the sensor for switching a circulating liquid into a first or second heat exchanger to either heat or cool the waste material.

Additional details of the invention will be disclosed in the following description, taken in connection with the accompaning drawings.

BRIEF DESCRIPTION OF THE FIGURES

FIG. 5 is a diagramatic view, parly in section, showing another embodiment of the present invention.

FIG. 6 is a cross sectional view of the embodiment shown in FIG. 5, taken along the line 6—6, looking in the direction of the arrows.

DESCRIPTION OF THE PREFEERRED EMBODIMENTS

Figure 1:
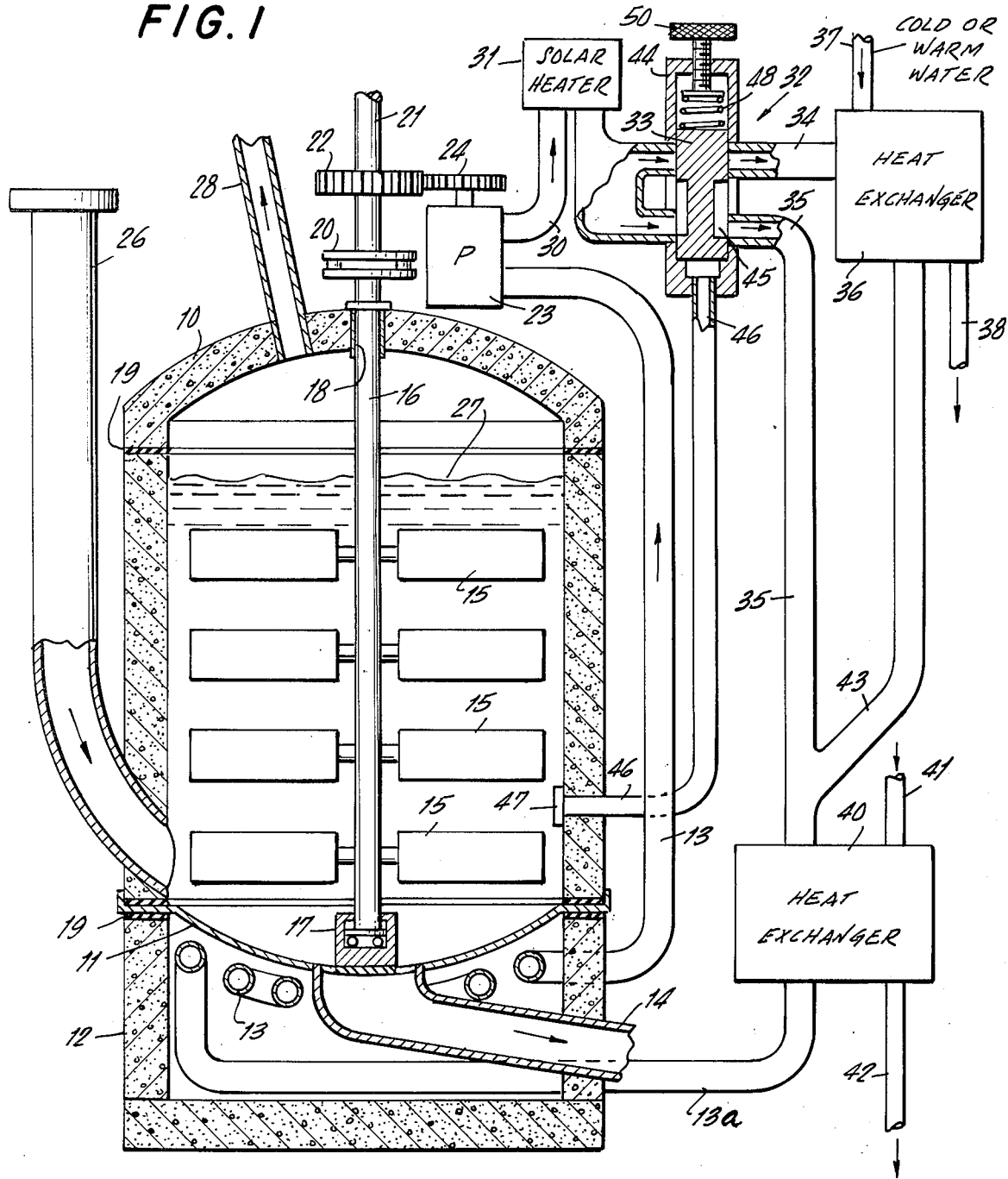
FIG. 1 is a diagramatic view, partly in section, of a preferred form of the apparatus.

Referring to FIG. 1, the gas generating apparatus comprises a container 10, preferably made with a cover of concrete, cylindrical side walls also of concrete, and a bottom 11 made of metal for fast heat transfer. The bottom 11 is mounted on a base 12 which surrounds a plurality of heating pipes 13 and provides space for an output discharge conduit 14 for removal of the digested material or sluge. A valve (not shown) is connected in series with the discharge conduit 14 for intermittent operation.

the container cover and the metal bottom 11 are preferably separated from the adjoining side walls by means of resilient washers 19.

Within the container 10, there is an arrangement of paddlewheels 15, preferably attached to a central shaft 16, supported at the bottom in a bearing 17, and extending through the top container cover in a second bearing 18, terminated by a flexible coupling 20. The flexible coupling 20 is secured to a power shaft 21 and gear wheel 22 which is used to transmit some of the shaft power to a liquid pump 23 by means of a second gear wheel 24. The power shaft 21 is preferably driven by a wind screw having inclined blades 25 (FIG. 3) for operation by a current of air.

The container 10 is charged by entering waste material into an entrance pipe 26, which deposits the material adjacent to a lower paddle wheel 15 so that it is at once stirred into the slurry mass. The decomposing action takes place throughout the slurry mass having an upper surface 27 just above the upper paddlewheels 15. As the methane and other gases are generated, they are released by the rotary paddle stirring action, rise to the surface, and are drawn off through pipe 28. Pipe 28 is connected to other chemical action components such as moisture absorbers and purifiers; devices well known in the art and not a part of this invention and therefore not shown.

The liquid pump 23 pumps a circulating liquid, which may be water, through an outlet pipe 30, then through a solar heating unit 31 where the liquid absorbs energy in the form of heat from the sun. The hot liquid is then forced through a two-way valve 32 having a sliding piston 33 and two output pipes 34 and 35. Pipe 34 conducts the hot liquid into a first heat exchanger 36 arranged to cool the liquid by the proximity of cold or moderately warm water. Introduced into and out of the exchanger by conduits 37 and 38. Pipe 35 conducts the hot liquid from the valve 32 to a second heat exchanger 40 where the liquid is subjected to an additional source of heat as herein more fully described. The output of the second heat exchanger 40 is delivered to conduit 13a which passes under the bottom 11 of the container and either heats or cools the slurry. The second heat exchanger 40 is connected to an external source of hot or cold water by means of conduits 41 and 42. Pipe 35 is joined by an output pipe 43 from the first heat exchanger 36 so that the second heat exchanger modulates the temperature of all the liquid passing through conduit 13 to the heater coils 13. After passing through the heating-cooling assembly the liquid is directed to the input port of the liquid pump 23 for continuous circulatory action.

The valve 32 includes a cylindrical casing 44 having two connected inlet ports on one side and two outlet ports on the other side connected to pipes 34 and 35. The valve piston 33 is formed with an annular cut out portion 45 which connects the input ports to either one of the output ports. At the lower end of the casing 44 a control conduit 46 is connected so that pressure within it positions the piston 33. The other end of conduit 46 is connected to a temperature responsive unit 47 which controls the pressure within the conduit 46. A spring 48 furnishes the return force acting against the pressure inside conduit 46 and its tension is adjustable by means of a manual screw 50.

The operation of the methane gas producer is as follows: Waste material, shredded or in granular form is introduced into the container 10 by way of the pipe 26 along with a liberal quantity of water. The container 10 should always be filled to a depth so that the upper surface 27 of the slurry is above the top paddlewheel 15. To insure a fast start in the decomposition action, anaerobic bacteria may be placed within the slurry when it is first assembled. At the start, with the paddle wheels turning and with the temperature of the slurry at about 70° F. (21° C.), heat must be added since the ideal temperature for anaerobic action is within the narrow range of 30° C. and 35° C. (85° and 95° F.). The decomposing action practically stops at temperatures below 15° C. and above 60° C. At 21° C. the temperature sensor 47 is set so that the piston 33 is in the position shown in FIG. 1 with the solar heater unit 31 connected through the valve 32 to pipe 35, the heat exchanger 40, and the heating coils 13. In order to get the action started quickly, hot water can be directed through pipes 41 and 42 to supplement the heat furnished by the solar heater 31. When the proper temperature is reached, the decomposition starts. Gas (nethane) is generated in the slurry due to the anaerobic bacteria action and some of the gas, in the form of small bubbles, moves directly to the surface 27 and to the space above the surface where it collects and can be drawn off through pipe 28. Other small bubbles of gas are entrapped in the slurry sludge and when enough gas bubbles are present, the sludge is lifted to the surface where it obstructs the passage of gas.

The revolving paddlewheels 15 perform several important functions in the operation of the gas producer: The wheels produce a mild mixing action so that the decomposition action is the same throughout the entire slurry. The stirring action breaks up the formation of sludge lumps and permits the entrapped gas bubbles to escape to the surface 27. The paddle rotation, moving in a dense slurry mixture generates considerable frictional heat which helps to maintain the proper operating temperature.

If the temperature of the slurry rises above the optimum range, the sensor 47 is activated and pushes the piston 33 up so that a portion of the circulating liquid from pump 23 passes into conduit 34 and the first heat exchanger 36 where it is cooled by cold water passing through pipes 37, 38. This portion of the circulating liquid is sent through pipe 43 and joined with other liquid to eventually enter the heater pipes 13 below the bottom 11 of the container. As shown in FIG. 1, the valve 32 may be designed so that the upper cutout portion 45 of the piston 33 opens up the entrance of conduit 34 at the same time the lower portion starts to cut off the flow to conduit 35. With the proper design, the flow of circulating liquid will remain constant regardless of the setting of the piston 33. A surge tank (not shown) may be connected to the circulating liquid system to compensate for loss of liquid by evaporation and to adjust for overall temperature changes.

Figure 2:
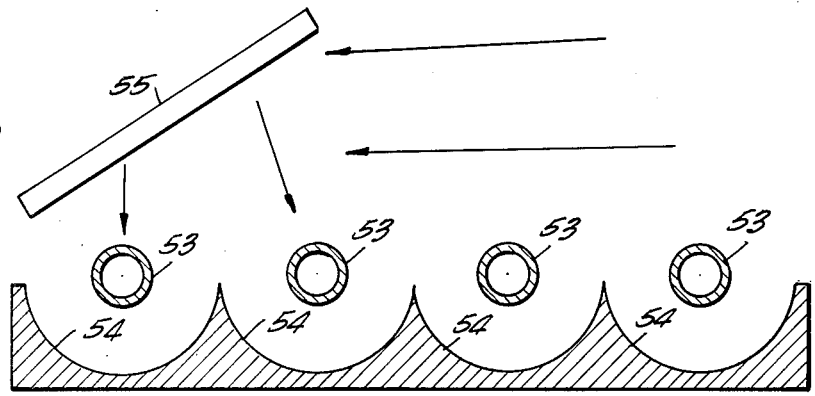
FIG. 2 is a cross sectional view of one form of solar heat absorber which may be employed to derive heat energy from the sun.

FIG. 2 shows one form of solar cell which may be used to convert the radiant energy from the sun to heat for raising the temperature of the slurry. A series of connected pipes 53, formed with black heat absorbing surfaces, are connected in series with pipe 30 and the valve input pipe. The pipes 53 are preferably mounted adjacent a series of reflector surfaces 54 so that a major portion of the radiant energy is directed upon the surface of the pipes. A movable reflector 55 turning in synchronism with the sun's movement relative to the earth, directs the radiant energy toward the pipe array at all times. Such mechanisms are well-known in the art.

Figure 3:
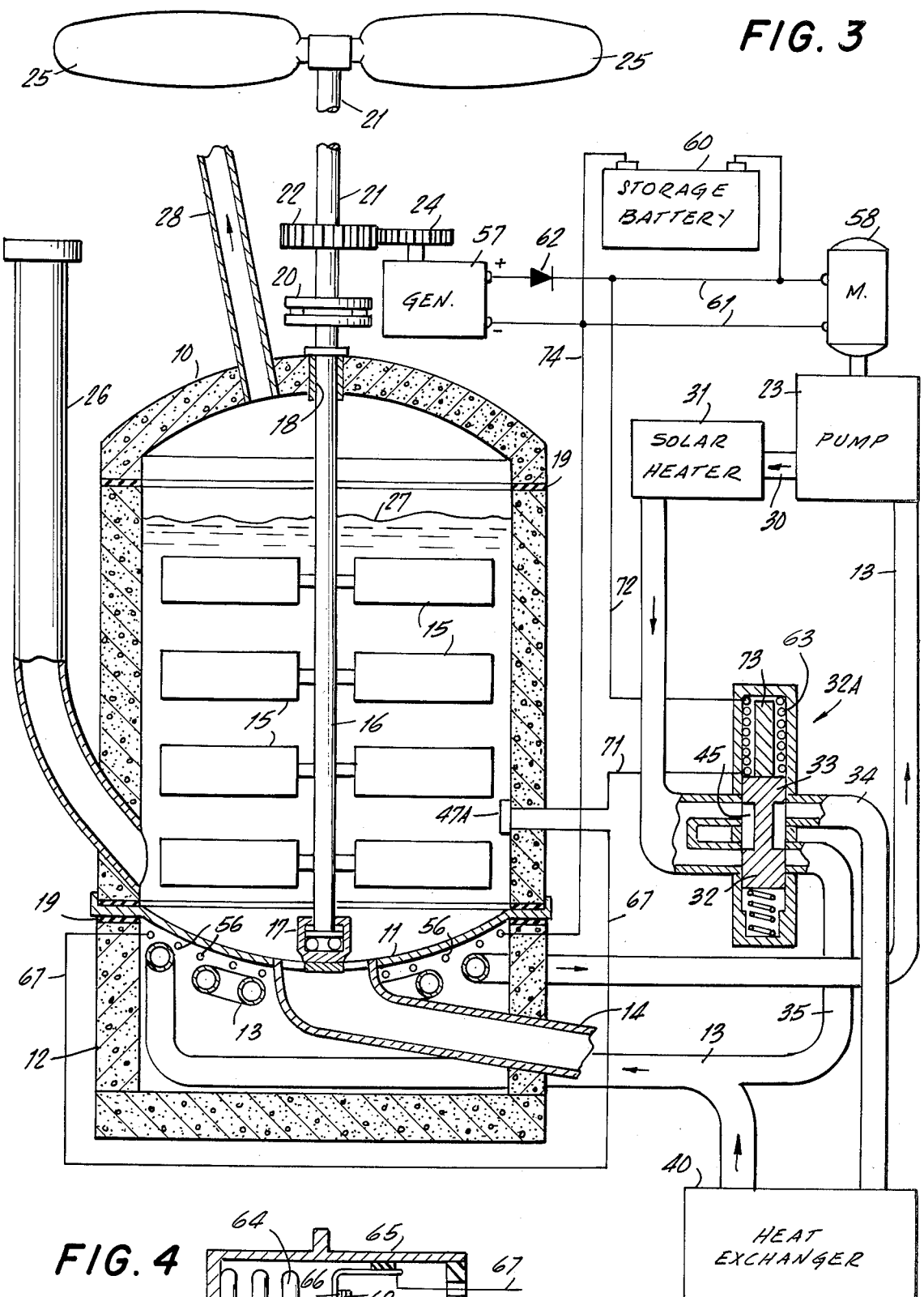
FIG. 3 is a view, similar to FIG. 1, of an alternate arrangement of components using a make-and-break electrical temperature sensor to maintain the temperature of the slurry within an optimum range.

FIG. 3 shows an alternate form of container for producing methane having many similar parts but controlled by electrical means and having an electrical resistance heater 56 under the container bottom 11 to aid in maintaining the proper operating temperature. Power for turning shafts 21 and 16 is derived from a wind screw 25 but other forms of mechanical energy may be utilized. Power is derived from shaft 21 as before by gear wheels 22, 24 but in this case, the gear 24 is coupled to an electric generator 57 which generates direct current power and applies it to a motor 58 coupled to the pump 23 which circulates the heating liquid through a valve 32A and a series of heating pipes 13. A storage battery 60 is connected across power lines 61 so that the battery can assume the load and maintain the motor running if the wind screw 25 drops below generating speed. A diode 62 is connected in series with the positive power line so that the current from the battery 60 cannot discharge through the generator when the generator voltage is reduced.

Figure 4:
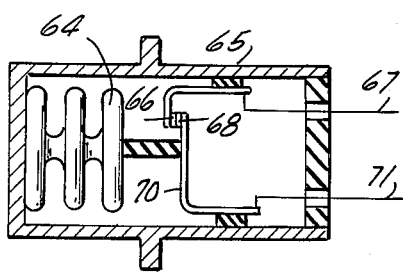
FIG. 4 is a cross sectional view of a make-and-break sensor which may be used with the apparatus shown in FIG. 3.

The temperature sensor 47A in this alternate form is a make or break contact array connected in series with the source of electric power, the heating coil 56, and a solenoid winding 63 in the two-way valve 32A. The contacts may be operated by a bimetallic strip, a column of mercury, or a bellows 64 (FIG. 4) filled with gas. All these temperature sensing devices are well-known in the art. The bellows type of sensor, shown in section in FIG. 4, includes a metal shell 65, a bellows 64 having a movable end coupled to a first contact 66 and a conductor 67. A second contact 68, in alignment with the first, is connected to a spring 70 and to a second conductor 71.

The operation of this thermostat array is as follows: When the temperature of the slurry is below a predetermined optimum value, contacts 66, 68 are closed and current flows from the positive line 61, over conductor 72 to the solenoid winding 63, attracting the core 73 and moving the piston 33 to its upper position. The circuit continues through the sensor contacts 66, 68. (FIG.4) then over conductor 67 to the resistance heater wires 56 under the bottom 11. From the heater wires the circuit is traced over conductor 74 to the other side of the power line 61. With the piston 33 in its upper position, as shown, circulating liquid from the solar heater 31 passes through the upper portion of the annular groove 45 and moves through conduit 34 to heat exchanger 40 where an additional amount of heat is added. The hot liquid is then directed through pipes 13 to raise the temperature of the slurry. As soon as the temperature reaches the optimum value, contacts 66, 68 are opened, the heater current through wires 56 is cut off, and the circulating liquid through the heat exchanger 40 is bypassed through conduit 35 by the piston falling to its lower position.

The action of the two-way valve 32A still provides a constant flow of circulating liquid through the solar heater 31 since the solenoid action insures that the piston 33 is either all the way up or all the way down.

The gas resulting from the fermentation is not all methane. The average amounts of gas from such an apparatus produces methane ($CH_4$) 65% carbon dioxide ($CO_2$) 30%, and nitrogen ($N_2$) 5%. Maintaining the temperature at the optimum value, 85° to 95° F., (29.5° to 35° C.) by the application of solar radiation and local heat units greatly increases the methane percentage and creates a more even flow of gas. The gas from conduit 28 should be stored in a constant pressure storage tank (not shown) so that the pressure above the slurry surface 27 does not rise above a predetermined value.

FIGS. 5 and 6 show another embodiment of the present invention. The main source of heat as illustrated in these Figures is the heat arising from the electric currents which are generated by the rotating magnets 100, 101 and 101a. These magnets are attached to shaft 16 by means of bolts 113. A cylinder 102 encloses shaft 16 and magnets 100, 101 and 101a. Because cylinder 102 has an inside diameter just larger than the length of said magnets shaft 16 and magnets 100, 101 and 101a can rotate freely within cylinder 102. Cylinder 102 is press fitted against bottom bearing 17 to prevent the slurry from leaking into it.

A paddle 108 is connected by a collar 115 which fits freely over cylinder 102, resting on bearings 107. When magnet 101a rotates, it pulls paddle 108 in rotation with it. As described above, the paddle 108 stirs the slurry and breaks up the solid matter in it while forcing bubbles of gas to rise to the slurry's surface 27.

The rotation of magnets 100 and 101 generates a magnetic flux inside cylinder 102 which is a conductor of electricity with a high permeability. Said flux (not shown) generates eddy currents in the cylinder. These currents heat the cylinder.

Having thus fully described the invention, what is claimed as new and desired to be secured by Letters Patent of the United States is:

1. Apparatus for the production of methane gas by biological decomposition of waste matter comprising;
   a. a container for holding waste material,
   b. an elongated shaft rotatably mounted within the container said shaft enclosed in an elongated electrically conductive cylinder and provided with magnets which are rotated with the shaft within the cylinder to generate electric eddy currents in the cylinder thereby providing a first heat source within the container to warm the waste material,
   c. paddle means coupled to the shaft within the container and in contact with the waste matter,
   d. at least one external heat source to raise the temperature of the waste matter within the container,
   e. a power source coupled to the shaft to rotate the said shaft and paddle wheels said paddle wheels providing a second heat source within the container,
   f. means to control the temperature of the waste matter within the container,
   g. means to introduce waste matter into the container, and,
   h. outlet means to remove the methane gas and excess heat from the container.

2. Apparatus according to claim 1 in which the power source for the second heat source is a wind driven screw mounted on the shaft outside the container.

3. Apparatus according to claim 1 in which the cylinder is made of a material of high electrical permeability.

4. Apparatus according to claim 3 in which the paddle means is freely mounted upon the cylinder and is driven by the rotating magnets attached to the shaft.

* * * * *